(12) United States Patent
Stern et al.

(10) Patent No.: US 10,126,215 B2
(45) Date of Patent: Nov. 13, 2018

(54) PATHOLOGIC STAGING COMPRESSION APPARATUS AND METHODS

(71) Applicant: Parker Isaac Instruments, LLC, Ithaca, NY (US)

(72) Inventors: Charles Stern, Ithaca, NY (US); Alex Bodell, Ithaca, NY (US)

(73) Assignee: Parker Isaac Instruments, LLC, Ithaca, NY (US)

( * ) Notice: Subject to any disclaimer, the term of this patent is extended or adjusted under 35 U.S.C. 154(b) by 99 days.

(21) Appl. No.: 15/348,666

(22) Filed: Nov. 10, 2016

(65) Prior Publication Data

US 2017/0059455 A1 Mar. 2, 2017

Related U.S. Application Data

(63) Continuation-in-part of application No. PCT/US2016/031743, filed on May 11, 2016.
(Continued)

(51) Int. Cl.
*G01N 1/28* (2006.01)
*A47J 19/00* (2006.01)
(Continued)

(52) U.S. Cl.
CPC .............. *G01N 1/286* (2013.01); *A47J 19/00* (2013.01); *B30B 9/047* (2013.01); *B30B 9/06* (2013.01);
(Continued)

(58) Field of Classification Search
CPC ..................................................... G01N 1/286
See application file for complete search history.

(56) References Cited

U.S. PATENT DOCUMENTS 2,419,545 A 4/1947 Gray et al.
3,682,092 A 8/1972 Breton et al.
(Continued)

OTHER PUBLICATIONS

Gehoff et al., "Optimal lymph node harvest in rectal cancer (UICC Stages II and III) after preoperative 5-FU-based radiochemotherapy. Acetone compression is a new and highly efficient method," Am J Surg Pathol 36(2):202-213, 2012.*
(Continued)

*Primary Examiner* — Rosanne Kosson
(74) *Attorney, Agent, or Firm* — Lerner, David, Littenberg, Krumholz & Mentlik, LLP

(57) ABSTRACT

A filtration assembly for separating solids from liquids contained in a sample, and a method for preparing such a sample are disclosed herein. According to one embodiment, the filtration assembly includes an inner element (100) with proximal and distal ends (102,103) and a sample (200) disposed therein. A reinforcing sleeve (300) is disposed around the inner element (100) to form a sample receiver (250) with proximal and distal ends (252,253). A filter (400) is disposed at the open proximal end of the sample receiver (252) and a filtrate receiver (500) is placed over the filter (400) and threadedly engaged with the sample receiver (250) to clamp the filter (400) therebetween. Then, the receivers (250,500) are inverted and a pressure is applied to the sample (200) to force a liquid component (200*a*) through the filter (400) into the filtrate receiver (500), while solids (200*b*) are retained in the sample receiver (250).

9 Claims, 10 Drawing Sheets

Related U.S. Application Data

(60) Provisional application No. 62/160,003, filed on May 12, 2015.

(51) Int. Cl.
    *B30B 9/26*     (2006.01)
    *B30B 9/04*     (2006.01)
    *B30B 9/06*     (2006.01)
    *G01N 1/10*     (2006.01)
    *G01N 1/06*     (2006.01)

(52) U.S. Cl.
CPC ............... *B30B 9/26* (2013.01); *G01N 1/06* (2013.01); *G01N 1/10* (2013.01); *G01N 1/2813* (2013.01); *G01N 2001/1025* (2013.01); *G01N 2001/1062* (2013.01)

(56) References Cited

U.S. PATENT DOCUMENTS

| | | |
|---|---|---|
| 4,050,373 A | 9/1977 | Hellmann |
| 4,263,330 A | 4/1981 | Streeter et al. |
| 4,744,926 A | 5/1988 | Rice |
| 4,953,109 A | 8/1990 | Burgis |
| 5,725,765 A | 3/1998 | Shen |
| 7,517,495 B2 | 4/2009 | Wu et al. |
| 8,177,968 B2 | 5/2012 | Wang |
| 8,323,490 B1 | 12/2012 | Wright et al. |
| 2003/0021736 A1 | 1/2003 | Kang et al. |
| 2007/0033731 A1 | 2/2007 | Blackburn |
| 2009/0293742 A1 | 12/2009 | Murphy et al. |
| 2013/0270161 A1 | 10/2013 | Kumar et al. |

OTHER PUBLICATIONS

Gehoff et al., "Optimal Lymph Node Harvestin Rectal Cancer (UICC Stages II and III) after Preoperative 5-FU-based Radiochemotherapy. Acetone Compression is a New and Highly Efficient Method," Am J Surg Pathol 36:2 (Feb. 2012).

Basten et al., "Acetonkompression Schnelle, standardisierte Methode zur Untersuchung von Lymphknoten im Gastrointestinaltrakt," Pathologe 3:31 (2010) pp. 218-224.

Haboubi et al., "The importance of combining xylene clearance and immunohistochemistry in the accurate staging of colorectal carcinoma," J Royal Soc Med 85 (Jul. 1992).

Lavy et al., A comparative study on two different pathological methods to retrieve lymph nodes following gastrectomy, http://www.journal-surgery.net/article/S1743-9191(14)00156-3/pdf (Jul. 2014).

Märkl et al., "The clinical significance of lymph node size in colon cancer," Modern Pathology 25 (2012) pp. 1413-1422.

Märkl et al., "Optimal Lymph Node Harvest in Neoadjuvantly Treated Colorectal Cancer Using Methylene Blue Assisted Lymph Node Dissection Technique," North Am J Med & Sci 6:2 (Apr. 2013).

Resch et al., "Pathological evaluation of colorectal cancer specimens: advanced and early lesions," Cesko-Slovenska Patologie 1 (2015).

Scheel et al.., "Comprehensive lymph node morphometry in rectal cancer using acetone compression," J Clin Pathol 0 (2015), pp. 1-7.

International Search Report from International Publication No. PCT/US2016/031743 dated Sep. 14, 2016.

\* cited by examiner

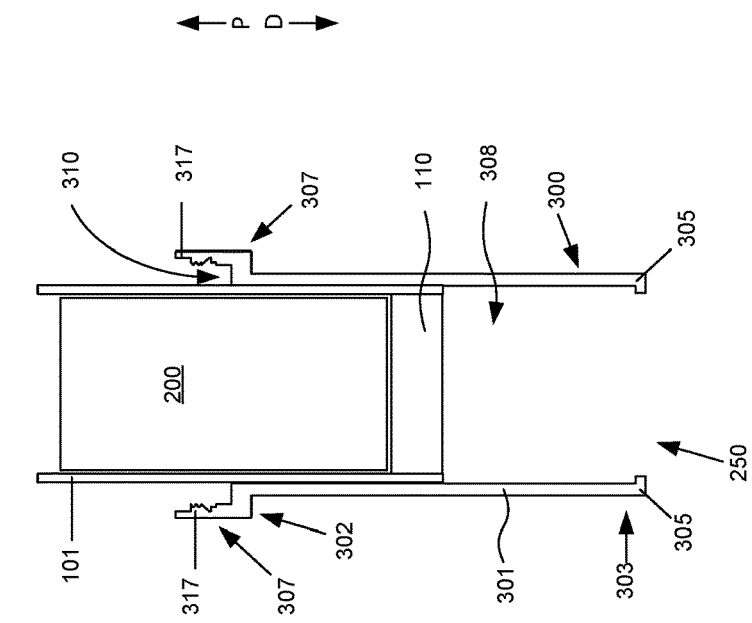
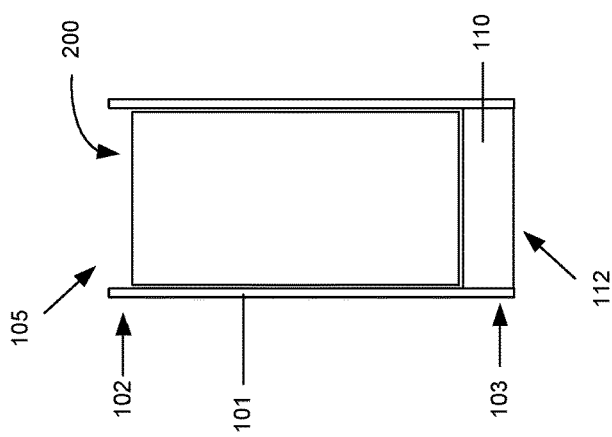
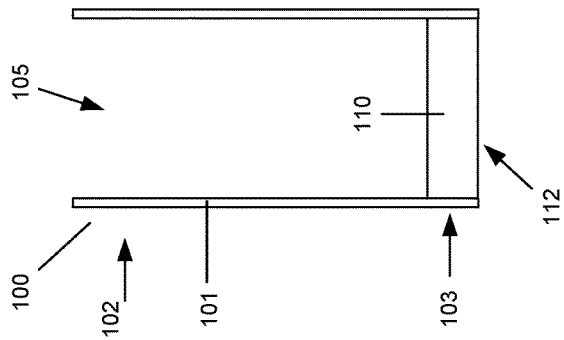

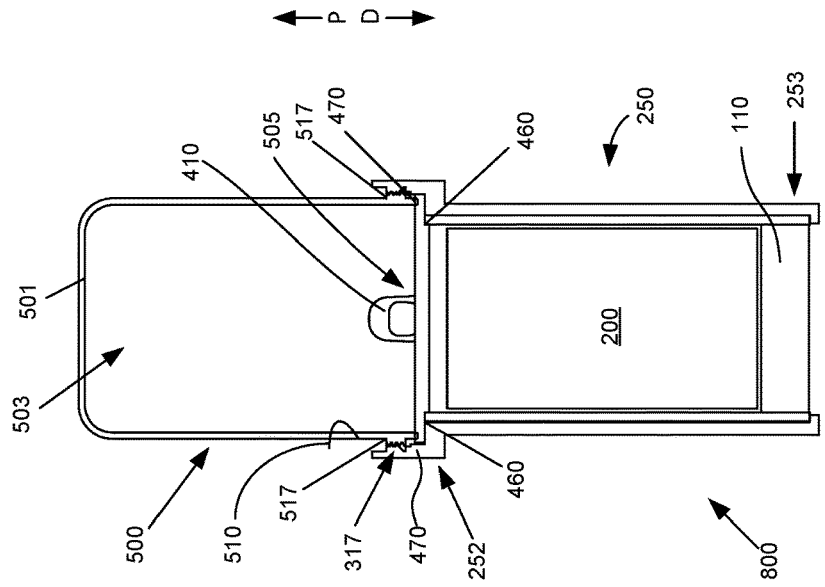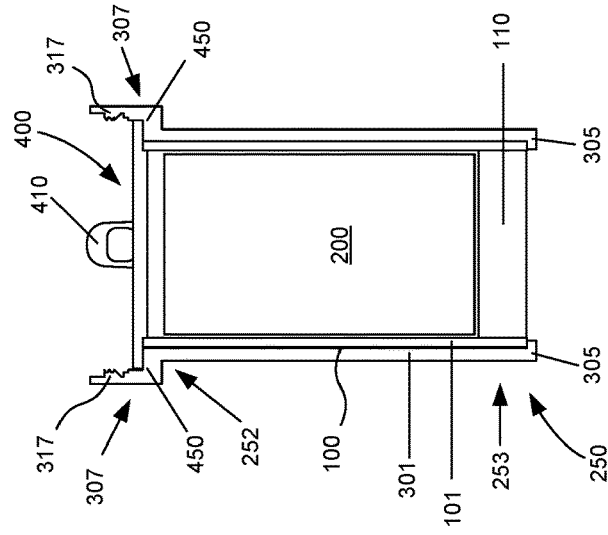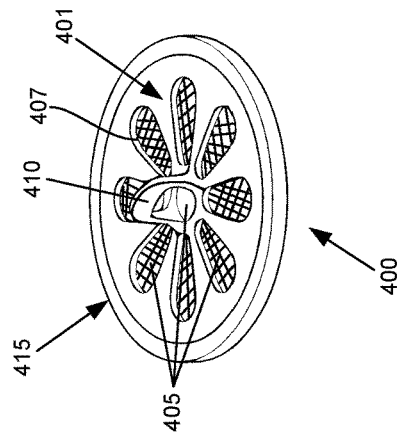

PATHOLOGIC STAGING COMPRESSION APPARATUS AND METHODS

CROSS-REFERENCE TO RELATED APPLICATIONS

The present application is a continuation-in-part of International Application No. PCT/US2016/031743, filed May 11, 2016, which claims the benefit of the filing date of U.S. Provisional Application No. 62/160,003, filed May 12, 2015, both of which are hereby incorporated herein by reference.

BACKGROUND OF THE INVENTION

The present invention pertains to apparatus and methods for preparing a sample such as a biological or pathologic sample for further examination by separating solids such as solid tissues from liquids contained in the sample.

Certain biological and pathological procedures require treatment of samples including solid tissues and a liquid phase, in order to remove the liquid phase. For example, such treatment is required in certain pathological staging procedures. The pathologic stage is a piece of diagnostic information relating to whether cancer has spread or "metastasized" in a patient having or suspected of having cancer. The pathologic stage is used in determining the patient's prognosis and treatment, including whether or not the patient will receive chemotherapy. Colorectal cancer typically metastasizes first to lymph nodes disposed in fatty tissue in the abdomen. Thus, examining these lymph nodes and adjacent fibrous tissue provides important information useful in determining the stage of colorectal cancer.

To determine the pathologic stage of colorectal cancer, the surgeon first resects a section of fatty tissue from the patient's abdomen. This fatty tissue is then sent to the surgical pathologist, whose responsibility is to determine the stage of the illness based on the extent of cancer observed within this tissue. Importantly, the pathologist is not interested in the fat itself, but rather in the fibrous tissue and lymph nodes that are contained within the fatty tissue.

In traditional staging methods, the pathologist meticulously dissects the fatty tissue with a scalpel in search of fibrous material and lymph nodes. The pathologist removes any clearly visible nodes or other relevant fibrous tissue for examination under the microscope. Inevitably, however, some very small or microscopic pieces of tissue are left behind. The presence or absence of any diagnostically relevant information (which may be microscopic) within the resected tissue may change the patient's prognosis and treatment. To account for this, the pathologist conventionally selects five to ten random samples from the tissue for microscopic study.

In recent years, a team of pathologists in Germany has pioneered a sample preparation technique that makes this process both more efficient and more accurate. This method is referred to as the "acetone compression method" or "ACM." The ACM is described in Gehoff et al., Am. J. Surg. Pathol., Vol. 36, pp. 202-213, 2012; Basten et al., Pathologe, Vol. 31, pp. 218-224, 2010; and Scheel et al., "Comprehensive lymph node morphometry in rectal cancer using acetone compression", J. Clin. Pathol., e-published Mar. 16, 2015, the disclosures of which are hereby incorporated by reference herein. The ACM allows the pathologist to eliminate the time-consuming dissection process while simultaneously avoiding the risk of missing diagnostically relevant tissue.

In practice of ACM, the pathologist first examines the fatty tissue sample for any large and clearly visible pieces of diagnostically relevant tissue. The pathologist then slices the sample into small (2 to 3 mm) sections and puts this material in acetone to soak overnight. Acetone dissolves lipids without affecting the integrity of fibrous tissue. The following day, the tissue is removed from the acetone bath. The sample as removed includes the tissue of interest together with acetone having lipids dissolved therein. This sample is loaded into a metal tube having a circumferential wall that is perforated with small (1 to 2 mm diameter) holes. The pathologist places the tube in an arbor press. The arbor press includes a lever linked through a rack and pinion mechanism to a ram. By pulling the lever manually, the pathologist forces the ram into the tube through one end while the other end of the tube is blocked, thereby compressing the sample in the tube. Compressing the sample forces the liquid phase including the fatty components to be extruded out of the small holes in the tube, leaving the solid components, including the fibrous tissue and lymph nodes in the tube. The pathologist has therefore reduced or eliminated diagnostically irrelevant information, i.e. fat, from the tissue sample. The solid tissue, and particularly the lymph nodes, is then examined by the pathologist to determine the presence or absence of metastases. Such examination may include, for example, morphological examination of the lymph nodes and microscopic examination after further processing such as sectioning and staining using known techniques. For accurate staging, it is desirable to examine a large number of lymph nodes.

ACM represents a more time-efficient approach for processing the tissue than conventional hand dissection. In addition, ACM eliminates the risk that the pathologist may overlook diagnostically relevant information, therefore increasing the accuracy of the pathologic staging process for cancers of this type. ACM is capable of providing double or even quadruple the number of lymph nodes, compared to the conventional technique of tedious dissection.

However, still further improvement would be desirable.

BRIEF SUMMARY OF THE INVENTION

One aspect of the invention provides methods of treating sample that include solid tissue and a solvent bearing fat dissolved from the solid tissue. A method according to this aspect of the invention desirably includes placing the sample in contact with a filter and applying pressure to the sample so as to force the solvent and fat through the filter while retaining the solid tissue on the filter and compress the solid tissue. The method according to this aspect of the invention desirably includes controlling the pressure-applying step so as to compress the solid tissue to a predetermined degree, and recovering the compressed solid tissue. The sample may be a pathological sample in which the solid tissue includes lymph nodes. For example, the solid tissue may include a section of fatty tissue from a patient having or suspected of having a cancer, such as a section of tissue from the abdomen of a patient having or suspected of having colorectal cancer. The method may further include examining the recovered solid tissue so as to derive an indication of the stage of the cancer. The method may still further include repeating the steps discussed above using samples derived from a plurality of patients, while compressing the solid tissue to the same degree in each repetition. The uniform compression applied to the tissues reduces sample-to-sample variation and thus facilitates accurate examination.

A further aspect of the invention provides filtration apparatus incorporating a sample receiver defining a bore with proximal and distal ends and a filter disposed at the proximal end of the sample receiver. The apparatus desirably also includes means for applying pressure to a sample contained within the bore so as to force a liquid component of the sample through the filter while retaining a solid component of the sample within the sample receiver and compress the solid component to a predetermined degree. The means for applying a pressure may include a piston disposed within the bore and means for applying a predetermined force to the piston so as to urge the piston toward the proximal end of the sample receiver.

A still further aspect of the invention provides a filtration assembly. The filtration assembly according to this aspect of the invention desirably includes a sample receiver having a hollow body defining a bore, a proximal end having a proximal opening, and a distal end, the bore extending distally from the proximal opening. The assembly desirably also includes a filtrate receiver having a hollow body defining an interior space and an opening communicating with the interior space and a filter disposed between the sample receiver and the filtrate receiver with the openings of the receivers facing the filter on opposite sides thereof. The assembly according to this aspect of the invention desirably includes a securement mechanism arranged to urge the receivers toward one another to thereby clamp the filter between the receivers and thereby form a seal between the proximal end of the sample receiver and the filter. In certain embodiments, the securement mechanism may include attachment features on the sample receiver and attachment features on the filtrate receiver, the attachment features of the receivers being engageable with one another. For example, wherein the attachment features may include threads on each of the receivers.

Yet another aspect of the invention provides a sample for use in a filtration assembly. The sample receiver according to this aspect of the invention desirably includes a hollow inner element defining a bore, a proximal end having a proximal opening, and a distal end, wherein the bore extends distally from the proximal opening and a piston disposed within the bore, and further includes a reinforcing sleeve releasably disposed around the inner element to prevent rupture of the inner element. As further discussed below, such a sample receiver may be used in a filtration assembly such as the filtration assembly discussed above. Substantial pressure may be applied within the internal element as, for example, when the receiver is used in the sample treatment method discussed above. The inner element may be an inexpensive tube formed from a polymer, whereas the reinforcing sleeve may be a relatively expensive reusable element. The inner element may be a disposable element that protects the reinforcing sleeve from contamination.

A still further aspect of the invention provides methods of processing a pathologic sample including solid and liquid components. The method according to this aspect of the invention desirably includes placing a sample into a sample receiver through an opening in the sample receiver while the opening faces upwardly, securing a filter over the opening of the sample receiver, then inverting the sample receiver and applying a pressure to the sample in the sample receiver to force a liquid component of the sample through the filter, and retrieving a solid component of the sample that is retained within the sample receiver. The step of securing a filter over the opening of the sample receiver may include securing a filtrate receiver to the sample receiver with the filter therebetween, such that the step of inverting the sample receiver also includes inverting the filtrate receiver. The step of securing a filtrate receiver to the sample receiver may include engaging a securement mechanism with the sample receiver and the filtrate receiver so as to clamp the filter between the filtrate receiver and the sample receiver.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

FIG. 1 is a sectional view of a component used in one embodiment of the present disclosure.

FIG. 2 is a sectional view of the component of FIG. 1 with a sample loaded therein.

FIG. 3 is a sectional view of the component and sample of FIGS. 1 and 2 being assembled with another component.

FIG. 4 is a perspective view of another component usable with the components of FIGS. 1-3.

FIG. 5 is a sectional view of the components of FIGS. 1-4 in a partially assembled condition.

FIG. 6 is a sectional view depicting an assembly including the components of FIGS. 1-5 together with a further component.

DETAILED DESCRIPTION

Figure 7:
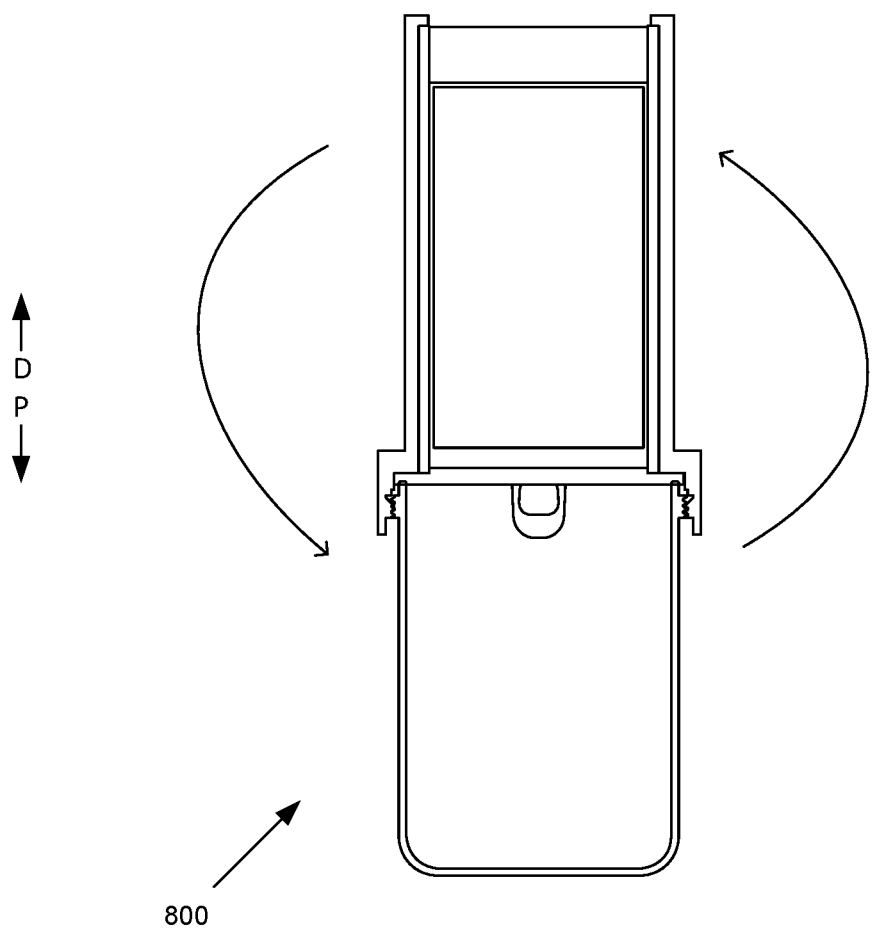
FIG. 7 shows the assembly of FIG. 6 in an inverted position.

A filtration assembly according to a first embodiment of the present disclosure includes a sample receiver 250, shown in an assembled condition in FIG. 5. The sample receiver includes an inner element 100 (FIG. 1). As best seen in FIG. 1, the inner element 100 has a hollow cylindrical body 101 with a bore 105, a proximal end 102, and a distal end 103. The volume of the bore varies depending on the size of the sample being prepared. However, for preparation of a tissue sample in staging of colorectal cancer, the bore typically has a volume of about 20 to 200 $cm^3$. Cylindrical body 101 may be formed from a polymer or metal resistant to the materials contained in the sample to be processed. For example, where the sample to be processed will include a solvent, the body should be resistant to attack by the solvent. Where acetone is used as the solvent, the body may be formed from a polymer such as nylon or acetal. A piston 110 is disposed within the bore 105 at the distal end 103 of the inner element 100. The piston 110 is in slideable, sealing engagement with body 101. Piston 110 may be formed primarily from a relatively rigid material such as a metal or a polymer resistant to the materials included in the sample as, for example, an acetal resin. The piston may be provided with compressible seals as, for example, compressible O-rings (not shown) forming the seal to body 101. Alternatively or additionally, the piston may have features such as a flexible lip (not shown) at its periphery. Such a lip may be formed integrally with the main structure of the piston. As depicted in FIG. 1, the piston is disposed at a starting position adjacent the distal end 103 of inner element 100. In the particular embodiment shown, the piston in its starting position is secured flush with the distal end 103 of the inner element 100 using an adhesive tape 112. The proximal end 102 of the inner element 100 is an open end.

The sample receiver 250 also includes a reinforcing sleeve 300 (FIG. 3). The reinforcing sleeve 300 similarly has a hollow cylindrical body 301, with an internal bore 308, a proximal end 302, and a distal end 303. Bore 308 is substantially open at both ends 302, 303 of the reinforcing sleeve 300. The proximal end 302 has a flat annular flange 310 projecting radially outwardly from bore 308 and has attachment features in the form of a collar 307 with internal helical threads 317 projecting extending in the proximal direction from flange 310. The reinforcing sleeve 300 is releasably disposed around the inner element 100 to prevent rupture of the inner element 100 during compression, as will be discussed below. The reinforcing sleeve may be made of an acetone resistant material such as aluminum or nylon, or from a metal such as aluminum or steel.

The distal end 303 of sleeve 300 has a locking feature 305 in the form of a flange 305 extending radially inwardly. Flange 305 partially overlies the distal end 103 of bore 308 in the sleeve. The internal diameter of bore 308 is just slightly larger than the external diameter of the body 101 of the inner element 100. For example, the internal diameter of the bore may be on the order of 0.05-0.15 mm larger than the outer diameter of body 101. The distance from flange 305 to flange 310 is just slightly less than the length of body 101, for example, about 0.5-2 mm less.

In the assembled condition of the sample receiver 250 (FIG. 5), inner element 100 is releasably received within the bore 308 of sleeve 300. When the inner element 100 is fully seated within the reinforcing sleeve 300, the distal end 103 of the inner element abuts the locking feature 305 (FIG. 5). In this condition, locking feature 305 locks the inner element against movement in the distal direction D, toward the bottom of the drawing in FIG. 5. In this assembled condition, the proximal end of tubular body 100 projects slightly in the proximal direction (toward the top of the drawing in FIG. 5).

The filtration assembly according to this embodiment also includes a filter 400 (FIG. 4). The filter 400 includes a circular backing plate 401 with holes 405 extending through it. In the middle of the plate 401 there is a finger grip 410 projecting from the plane of the plate of the proximal or downstream side of the plate, seen in FIG. 4. Backing plate 401 desirably is substantially rigid, and typically is formed from a metal such as stainless steel. A mesh 407 overlies the distal or upstream side of the plate at least in the area of the plate where holes 405 are present. The mesh 407 may be a stainless steel mesh. A gasket 415 formed from a relatively soft material such as an elastomer or polymer resistant to the solvent in the sample is provided around the periphery of the plate, on both sides of the plate.

The filtration assembly further includes a filtrate receiver 500 (FIG. 6). The filtrate receiver 500 has a cup-like hollow body 501 with an interior space 503 and an opening 505. As shown, filtrate receiver 500 is a cup. The body 501 has a small aperture 510 extending through it adjacent opening 505. The body 501 also has attachment features 517 in the form of external threads engageable with the threaded attachments 317 on the reinforcing sleeve 300 of the sample receiver 250.

The components described above can be assembled as shown in FIG. 6. In the assembled condition, the filter 400 is disposed between the sample receiver 250 and the filtrate receiver 500, with the proximal or downstream side of the filter facing toward the filtrate receiver and with finger grip 410 projecting into the filtrate receiver through the opening 505. The upstream or distal side of the filter faces toward the sample receiver, with the gasket 415 aligned with the wall of inner component body 101. The threads 517 of the filtrate receiver are engaged with the threads 317 on the sleeve 300 of the sample receiver 250. By rotating the filtrate receiver relative to the sleeve, the filtrate receiver is brought into forcible engagement with the filter 400, so that the filter is tightly clamped between the filtrate receiver and the sample receiver. In this condition, the inner component body 101 bears on filter 410 through gasket 415, and thus forms a fluid-tight seal with the filter.

Figure 8:
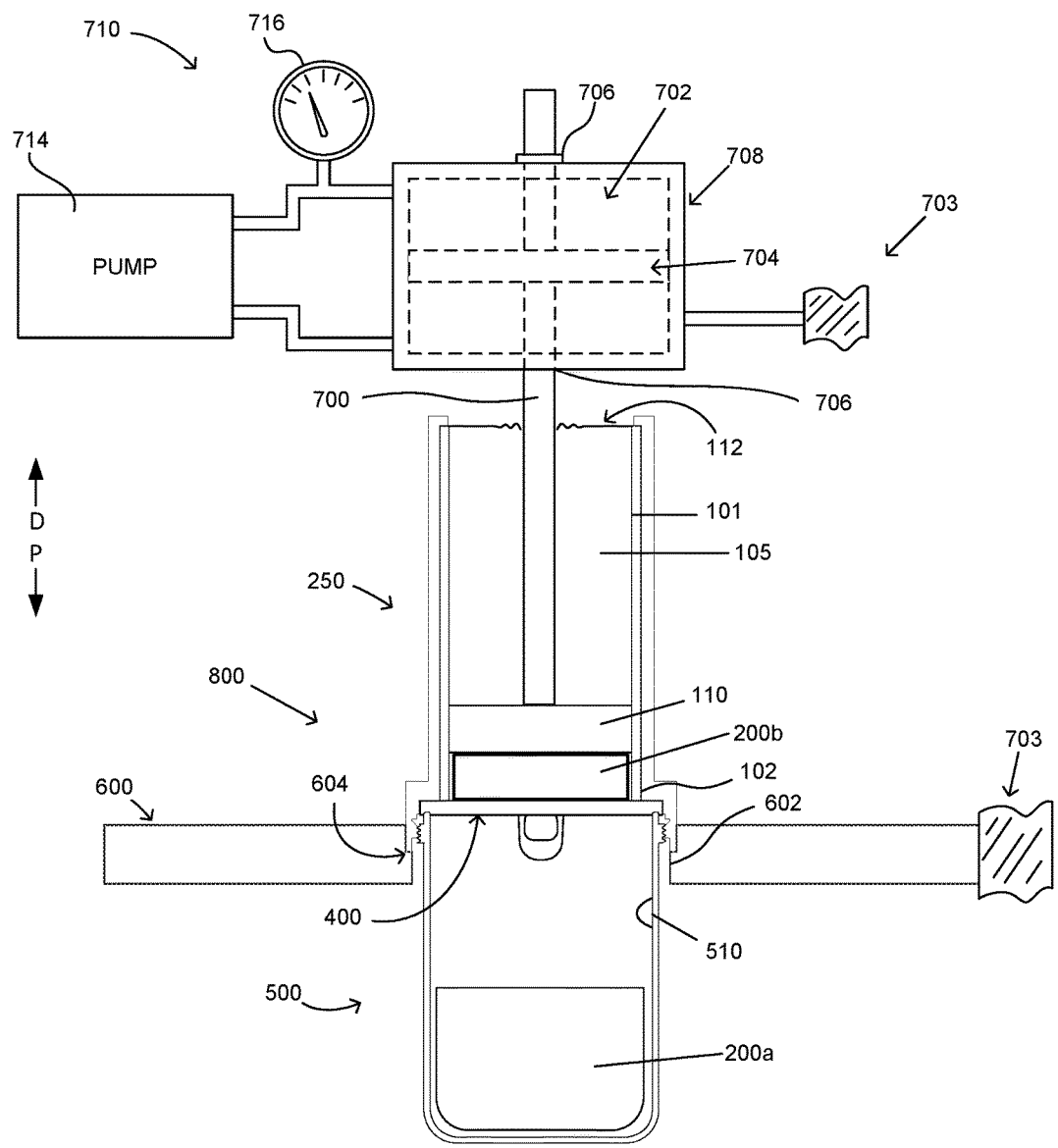
FIG. 8 is a partially diagrammatic, partially sectional view depicting an apparatus including the assembly of FIGS. 6 and 7 and other components.

The filter assembly 800 can be used in conjunction with a press (FIG. 8). The press includes a frame 703, only partially depicted in FIG. 8 for clarity of illustration, and positioning plate 600 mounted to the frame. The positioning plate has a hole 602 adapted to hold the filter assembly 800 in a predetermined position relative to the frame. In this embodiment, the hole 602 is adapted to engage the collar 307 of sleeve 300, and to hold the filter assembly with the filtrate receiver 500 disposed below the plate. The positioning plate has a ledge 604 adapted to abut the proximal end of the collar 307 and thus support the sample receiver 250. The press further includes a force-applying element in the form of a ram 700 mounted to the frame 703 for movement along a path coaxial with the hole 602 in the positioning plate. The press further includes an actuator 710 adapted to urge ram 700 downwardly with a predetermined force. In this embodiment, the actuator includes a hydraulic cylinder having a chamber 702 defining a bore and a piston 704 in slideable sealing engagement with the bore. Piston 704 is fixed to ram 700. In this embodiment, the chamber 702 is fixed to frame 703 and has conventional bearing and seal assemblies 706 at its top and bottom ends. The ram 700 extends through the chamber and is slideable in bearing and seal assemblies 706. Actuator 710 further includes a manually controllable pump 714 connected to the reservoir and to chamber 708. The pump is arranged to either force fluid into chamber 708 above piston 704 while allowing fluid in the chamber below the piston to drain back into the pump so as to drive the ram downwardly. The pump is also arranged to reverse this action so as to drive the ram upwardly. A transducer in the form of a pressure gauge 716 is connected to the chamber so that the pressure gauge will indicate the pressure of fluid above piston 704. As the downward force applied to ram 700 by the hydraulic fluid is directly related to the pressure, the reading on pressure gauge 716 will constitute a signal directly related to the force applied to the ram during downward movement.

In operation, in a method according to a further embodiment of the present disclosure, the compression assembly and press described above are used to treat a sample including a solid tissue and a solvent bearing fat dissolved from the solid tissue. The solid tissue includes lymph nodes. In this embodiment, the sample is a preparation derived by treating a section of fatty tissue from the abdomen of a patient having or suspected of having colorectal cancer with a solvent such as acetone so as to dissolve fat from the solid tissue. The sample may be prepared by cutting the tissue into pieces and contacting the pieces with acetone, typically for a prolonged period such as overnight, generally as discussed in the aforementioned articles teaching ACM.

The inner element 100 of the sample receiver is initially in the starting position as depicted in FIG. 1, with the open proximal end 102 of the inner element facing upwardly. While the inner element is in this position, the sample 200 is loaded through the open proximal end 102 of the inner element 100 into the bore 105. After loading, the inner element 100 is fully inserted into the reinforcing sleeve 300 such that the distal end 103 abuts the locking feature 305, thereby completing assembly of the sample receiver 250.

Next, the filter 400 is placed over the open proximal end 252 of the sample receiver 250 and the compression seal 450 is formed between the filter 400 and the reinforcing sleeve 300. The filtrate receiver 500 is placed over the filter such that the openings 505,252 of the receivers are facing the filter 400 opposite each other. The threads on the reinforcing sleeve 317 engage the threads on the filtrate receiver 516 so as to urge the receivers 250,500 towards one another, clamping the filter 400 between the receivers 250,500 (FIG. 6). This creates a first clamp seal 460 between the filter 400 and the proximal end 102 of the inner element 100, and a second clamp seal 470 between the filter 400 and the filtrate receiver 500, thus bringing the filtration assembly 800 to its assembled condition.

The assembly 800 is then inverted (FIG. 7) so that the opening of the filtrate receiver 505 and the open proximal end of the sample receiver 252 face downwardly. While ram 700 is in a retracted position remote from the positioning plate 600, the filtration assembly is placed in positioning plate 600 of the press (FIG. 8). Pump 714 of actuator 710 is operated to force hydraulic fluid under pressure into chamber 708 above piston 704. The pressurized fluid forces ram 700 downwardly until the ram encounters piston 110 at the distal end 103 of the sample receiver. The ram moves the piston toward the proximal end 102 of the sample receiver and toward filter 400. The force applied to the ram by the piston 110 applies pressure to the sample, and thus forces the liquid component 200*a* of the sample through the filter 400 and into the filtrate receiver 500. The solid component of the sample 200*b* is retained within the sample receiver 250. As the liquid component of the sample enters the filtrate receiver 500, air flows out of the of the filtrate receiver 500 and through the aperture 510 to maintain the pressure within the filtrate receiver at or near atmospheric pressure.

As pressure is applied to the sample within the inner element 100 of the sample receiver, the inner element 100 tends to expand radially. Reinforcing sleeve 300 reinforces the inner element 100 and limits any such expansion. As mentioned above, the reinforcing sleeve is closely fitted around the inner element 100. As the inner element expands radially, the wall of the inner element comes into contact with the reinforcing sleeve. The sleeve counteracts the pressure within the inner element, and keeps the inner element from expanding radially to such a degree that the seal between the inner element 100 is broken, or to such a degree that the inner element ruptures.

The seal between the inner element and the filter prevents leakage of the sample out of the filtration assembly, and also keeps the sample out of contact with the sleeve so that the reinforcing sleeve is not contaminated by the sample. Typically, all of the liquid forced out of the sample is contained within the filtrate receiver, so that the solvent and fat from the sample do not contaminate the surrounding area.

The amount of pressure applied to the sample 200 is controlled by monitoring the pressure of the hydraulic fluid. As mentioned above, the force applied to urge the ram 700 and piston 110 of the sample receiver in the proximal direction is directly related to the pressure applied to the hydraulic fluid. By monitoring gauge 716, the operator can control operation of the pump so as to maintain the hydraulic fluid pressure at a predetermined level and thus maintain the force applied to piston 110 at a predetermined level so as to compress the solid component of the sample 200*b* to a predetermined degree. Typically, for a tissue sample of the type used in this embodiment, the pressure applied to the sample is about 500 to about 2500 pounds per square inch (about 3500 to about 14000 kPa). That is, the magnitude of the force applied to the piston 110 by the ram 700 is monitored and in response, an actuator is controlled such that the force does not exceed a predetermined force.

After compression, the ram 700 is retracted and assembly 800 is removed from the positioning plate 600. The filtrate receiver 500 is detached from the sample receiver 250. Still, the liquid component of the sample 200*a* is safely confined in the filtrate receiver 500. The liquid component typically is transferred to a storage container (not shown) for safe disposal or reclamation of the solvent as, for example, by distillation.

After the filtrate receiver is removed, the filter 400 is removed by pulling it away from the sample receiver, using finger grip 410. Then, the solid component of the sample 200*b* is retrieved by hand from the sample receiver 250. For example, the piston can be pushed farther in the proximal direction by inserting a rod (not shown) through the open distal end 103 of the inner component 100 so as to eject the sample from the inner component through the open proximal end 102 of the inner component 100. The sample may be removed before or after removing the inner element from the reinforcing sleeve, and before or after removing the sample receiver from the positioning plate.

The solid component of the sample is then examined. Such examination may include identification of lymph nodes included in the solid component and conventional macroscopic or microscopic examination of the lymph nodes so identified. The solid component of the sample, or lymph nodes recovered from the solid component, may be subjected to conventional processing steps such as fixation and staining. The results of such examination can be used to determine the presence or absence of malignancy in the lymph nodes. This information can be used in the conventional manner to determine whether the patient is suffering from colorectal cancer and, if so, the stage of the disease. Typically, the method steps discussed above are repeated many times over, with many samples derived from many different patients. In each repetition, the pressure applied to the sample is controlled to the same predetermined value, so as to compress the solid component of each sample to the same degree. In the embodiment discussed above, the operator monitors the pressure gauge and controls the pump to apply the same hydraulic fluid pressure during the compression step. Compressing all of the samples to the same degree minimizes differences between the samples in the morphology of the lymph nodes caused by the compression procedure. This facilitates consistent identification and examination of the lymph nodes.

Desirably the reinforcing sleeve 300 is reusable, whereas the inner element 100 is disposable. The inner element can be removed from the reinforcing sleeve 300 and a new inner element can be inserted during each repetition. Because the inner element isolates the sample from the reinforcing sleeve during each repetition, there is little or no chance of crosscontamination between samples processed in different repetitions. The piston 110 desirably is also disposable.

In the embodiment discussed above with reference to FIG. 1-8, the securement mechanism that urges the filtrate receiver and sample receiver toward one another so as to clamp the filter between them includes attachment features in the form of threads on the sleeve of the sample receiver and on the filtrate receiver. However, other mechanisms can be used. For example, a filtration assembly 1800 according to a further embodiment (FIG. 9) includes a sample receiver 1250 incorporating a reinforcing sleeve 1300 and an inner element 1100 generally similar to those discussed above. In this embodiment, the inner element 1100 has a flange 1102 at its proximal end, whereas the reinforcing sleeve is 1300 is a tube with plain open ends. The filtrate receiver 1500 has a flange 1502 around its opening 1505. The securement mechanism includes a clamp 1000 separate from the filtrate and sample receivers. Clamp 1000 includes a first ring 1002 with a collar 1006 bearing female threads and an annular lip 1004 projecting inwardly from the collar. The clamp also includes a second ring 1010 with a collar 1012 bearing male threads engageable with the threads of the first ring 1002. Second ring 1010 also has an inwardly projecting lip 1014. In the assembled condition, the lip 1014 of the second collar overlies the flange 1502 of the filtrate receiver, and the lip 1004 of the first collar overlies the flange 1102 of the sample receiver inner element. Here again, the filter 1400 is disposed between the filtrate receiver and the sample receiver. The collars are rotated relative to one another so as to engage the threads with one another and force the collars toward one another, thus urging the flanges of the receivers toward one another and clamping the filter 1400 between the receivers.

In this embodiment, sleeve 1300 may be fitted around the inner element 1100 of the sample receiver after the first collar is assembled with the inner element. This step may be performed before or after assembling the inner element with the filtrate receiver, clamp, and filter.

In this embodiment, the filter 1400 does not include a soft element or gasket around its periphery. Instead, a separate gasket 1415 is interposed between the flange 1102 of the sample receiver and the filter, so that the sample receiver bears on the filter through the gasket. Stated another way, it is not essential that that either receiver directly contacts the filter.

Figure 9:
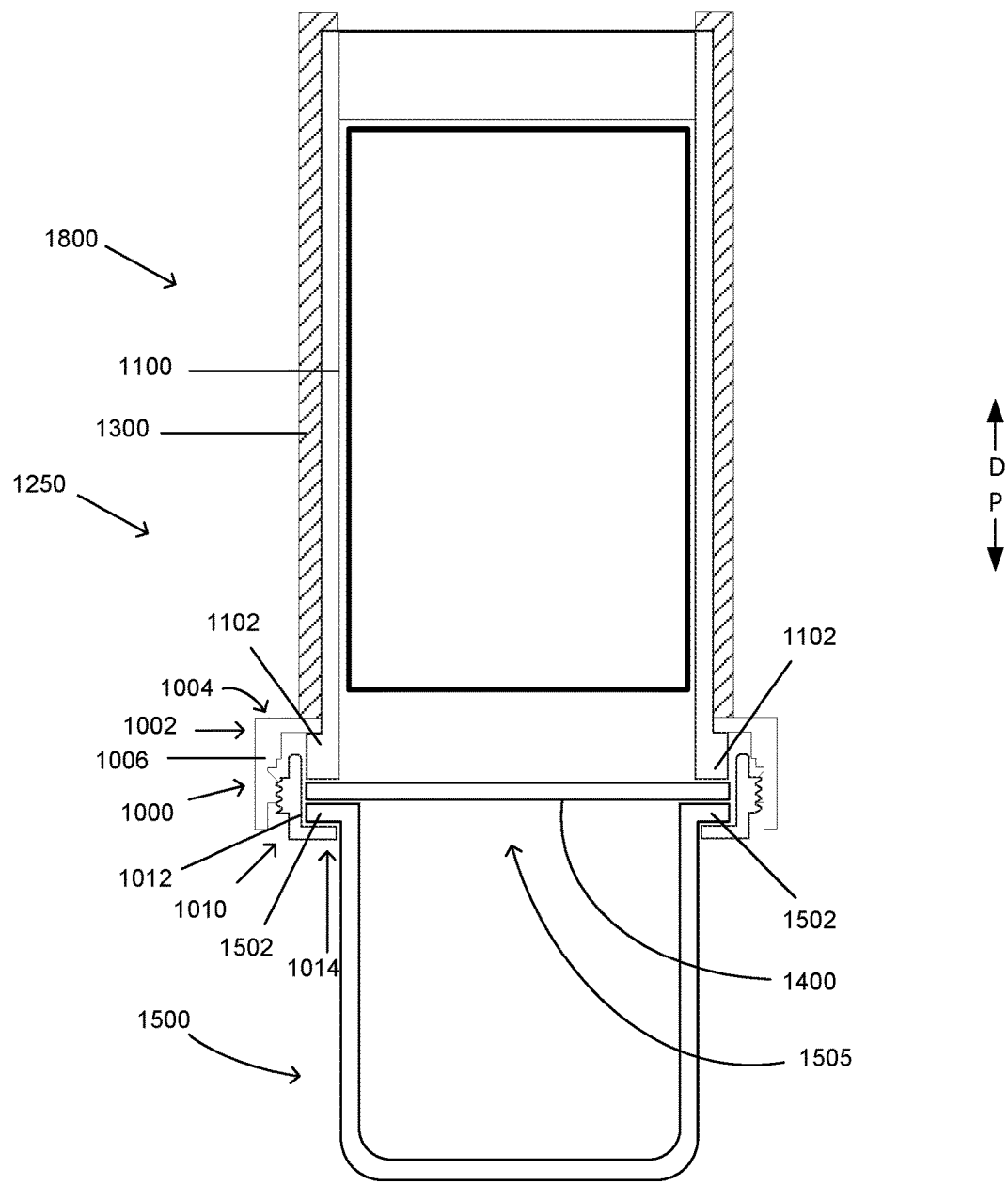
FIG. 9 is a sectional view depicting an assembly according to another embodiment.
Figure 10:
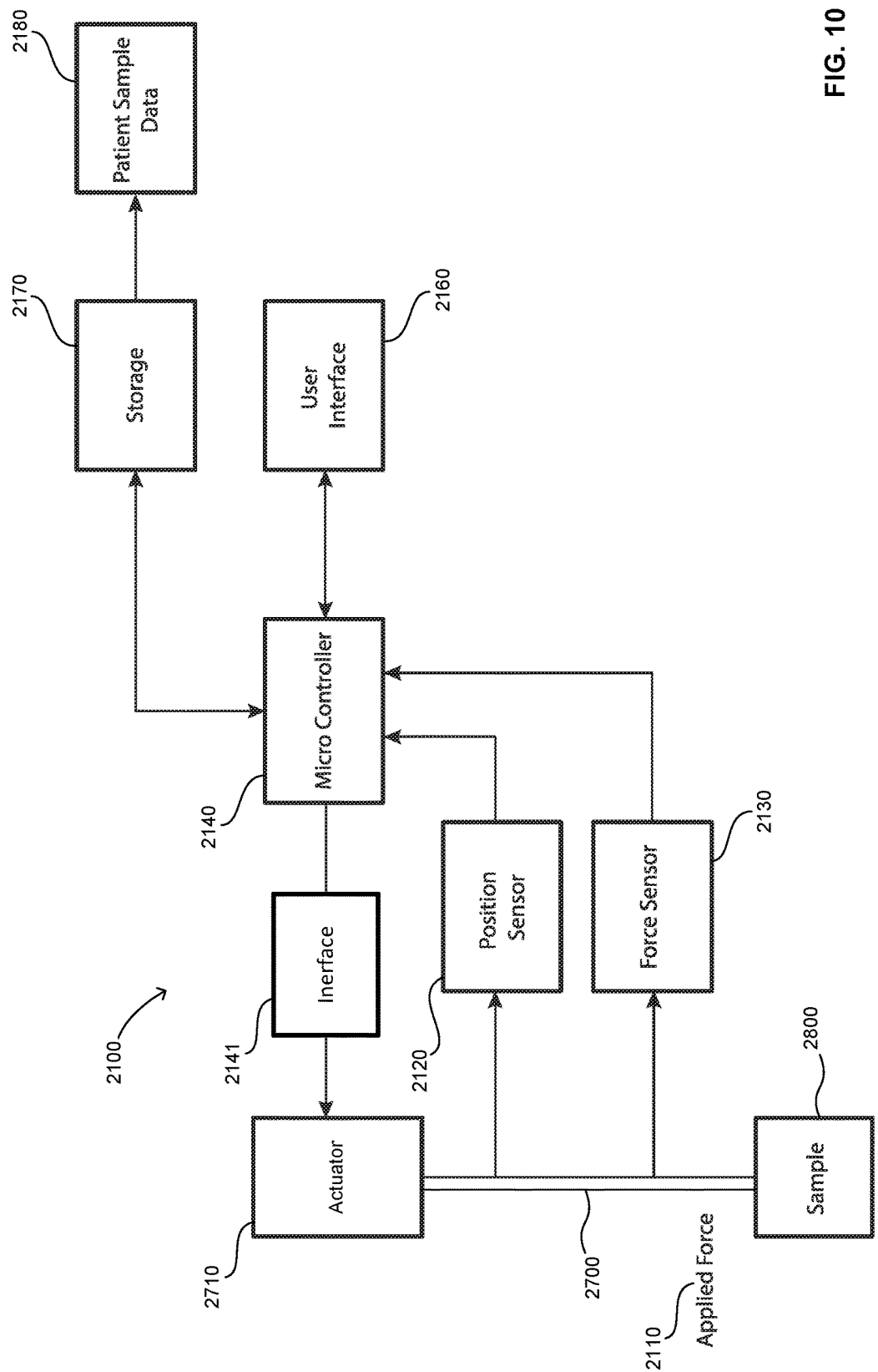
FIG. 10 is a block diagram depicting an apparatus according to a further embodiment.

Also, in the embodiment of FIG. 9, the filtrate receiver does not incorporate a vent opening. The downstream surface of filter 1400, or the surface of flange 1502, or both, may be roughened so that they do not form a seal with the downstream surface. Thus, air inside the filtrate receiver may escape at the interface between the filtrate receiver and filter as liquid is forced into the filtrate receiver during operation. These features also can be used in the embodiment of FIGS. 1-9.

The assembly of FIG. 9 can be used in the methods discussed herein in essentially the same manner as the assembly of FIGS. 1-8.

The securement mechanism need not incorporate threaded elements. Other mechanical elements capable of exerting forces to urge the receivers toward one another, such as toggle mechanisms, latches, cam-operated mechanisms and the like may be employed instead of threaded elements. These elements may be used either as a separate clamp or as attachment elements carried on one or both of the receivers.

In the embodiments discussed above, the sample receiver includes an inner element separate from the reinforcing sleeve. However, the sample receiver may be formed as a single component with attachment features that engage with the filtrate receiver.

In the embodiments discussed above, the hydraulic actuator 710 serves as a means for applying a force to a piston that compresses a sample. The force applied by the actuator is controlled to have a predetermined magnitude by monitoring of the signal from the pressure transducer or gage 716 and terminating operation of the pump when the signal indicates that the pressure of the hydraulic fluid, and hence the force applied to the piston in the sample receiver, has reached a predetermined level. However, this arrangement may be varied. Other actuators capable of applying a force can be used. Examples of such other actuators include electrically driven actuators, pneumatically driven actuators and gravity-driven actuators. One form of electrically driven actuator includes an electric motor having an output shaft, the motor being arranged to apply a torque to rotate the output shaft. The output shaft of the motor may be linked to the force-applying element such as the ram of a press by a mechanical linkage such as a gear train, rack and pinion, cam or screw arrangement which converts rotation of the shaft to linear motion of the ram, and thus converts the torque applied through the shaft into a force urging the ram in a forward linear direction. The combination of motor and linkage is commonly referred to as a "linear actuator." Other electrically driven actuators include linear electromagnetic actuators such as solenoids and linear electric motors. Pneumatically and hydraulically driven actuators include, for example, conventional pneumatic and hydraulic cylinders, bellows, and rotary pneumatic motors. Yet another type of actuator that may be employed is a gravitationally driven actuator including a mass linked to the force-applying element so that the weight of the mass urges the force-applying element in the forward direction, toward the proximal end of the sample receiver. For example, the mass may be mounted on a lever or other mechanical linkage that is connected to the force-applying element so that the force applied is many times the weight of the mass.

The actuator may be controlled by an automatic feedback control system that automatically monitors a signal from a transducer representing the force applied to the piston and hence the pressure applied to the sample, and automatically controls the actuator to provide the desired predetermined force and predetermined pressure. The transducer may derive the signal by monitoring an input to the actuator, such as the pressure of hydraulic fluid or gas applied to a hydraulic or pneumatic actuator, or the voltage or current supplied to an electrically driven actuator. Alternatively, the transducer may derive the signal by measuring an output of the actuator, such as the force applied by the force-applying element or a force or torque exerted at an intermediate point in a linkage connecting the actuator with the force-applying element. The transducer also may be arranged to measure the pressure within the sample receiver directly.

The feedback control system may execute a simple "on-off" control scheme, as by terminating application of the force to the piston when the force or pressure reaches a set threshold. In a further variant, the feedback control system may control the actuator to maintain the force or pressure within a predetermined tolerance band of a preset value for a predetermined time. Such control may be executed through repeated on-off cycles so as to maintain the force or pressure as the liquid component slowly drains from the sample receiver through the filter. Alternatively, such control may include a proportional-integral-derivative feedback loop, which derives an error signal related to one or more of the difference between the actual force or pressure and the preset value, the integral of such difference, and the derivative of such difference. The error signal is applied to modify an input to the actuator as, for example, the voltage or current applied to an electrically driven actuator.

In some instances, the actuator may be arranged to apply a predetermined force without feedback control. For example, a gravitationally driven actuator will inherently apply a force proportional to the weight of the mass, so that the force may be set to a predetermined magnitude by selecting the mass. In another example, a hydraulic or pneumatic actuator can be connected to a valve set to open at a predetermined pressure, so that the pressure applied in the actuator cannot exceed the predetermined pressure. Such a valve is commonly referred to as a "pop-off" valve or "safety valve". In such an embodiment, the pump or other source of pressure may be operated so as to keep the valve open, thus applying the predetermined pressure to the sample.

In the embodiments discussed above, the degree to which the solid components of the sample are compressed is controlled by application of a predetermined pressure. Alternatively or additionally, the degree of compression can be controlled by controlling the travel of the element that compresses the solid components. For example, the feedback control system may include a transducer that monitors the travel of the piston in a sample receiver as discussed above. Such monitoring may be direct or indirect as, for example, by monitoring the travel of the element that applies force to the piston or the motion of another element mechanically linked to the force-applying element. The control system may be arranged to terminate application of the compressing force when the piston has moved through a predetermined travel. In another alternative, the actuator may incorporate a mechanical stop to limit travel of the force-applying element to a predetermined value. Likewise, the filtration assembly may include a stop to limit travel of the piston.

As discussed above, it is desirable to compress the solid components of the various samples to the same degree. However, in some instances it may be desirable to treat samples in different categories differently. For example, it may be desirable to compress all samples taken from adult patients to one degree of compression, and compress all samples from children to another degree of compression. In another example, it may be desirable to compress samples that include a more viscous liquid phase for a longer time than samples that include a less viscous liquid phase, so as to achieve the same degree of compression in all of the samples. An automatic feedback control system may accommodate different user-selectable settings to provide different degrees of compression.

Figure 11:
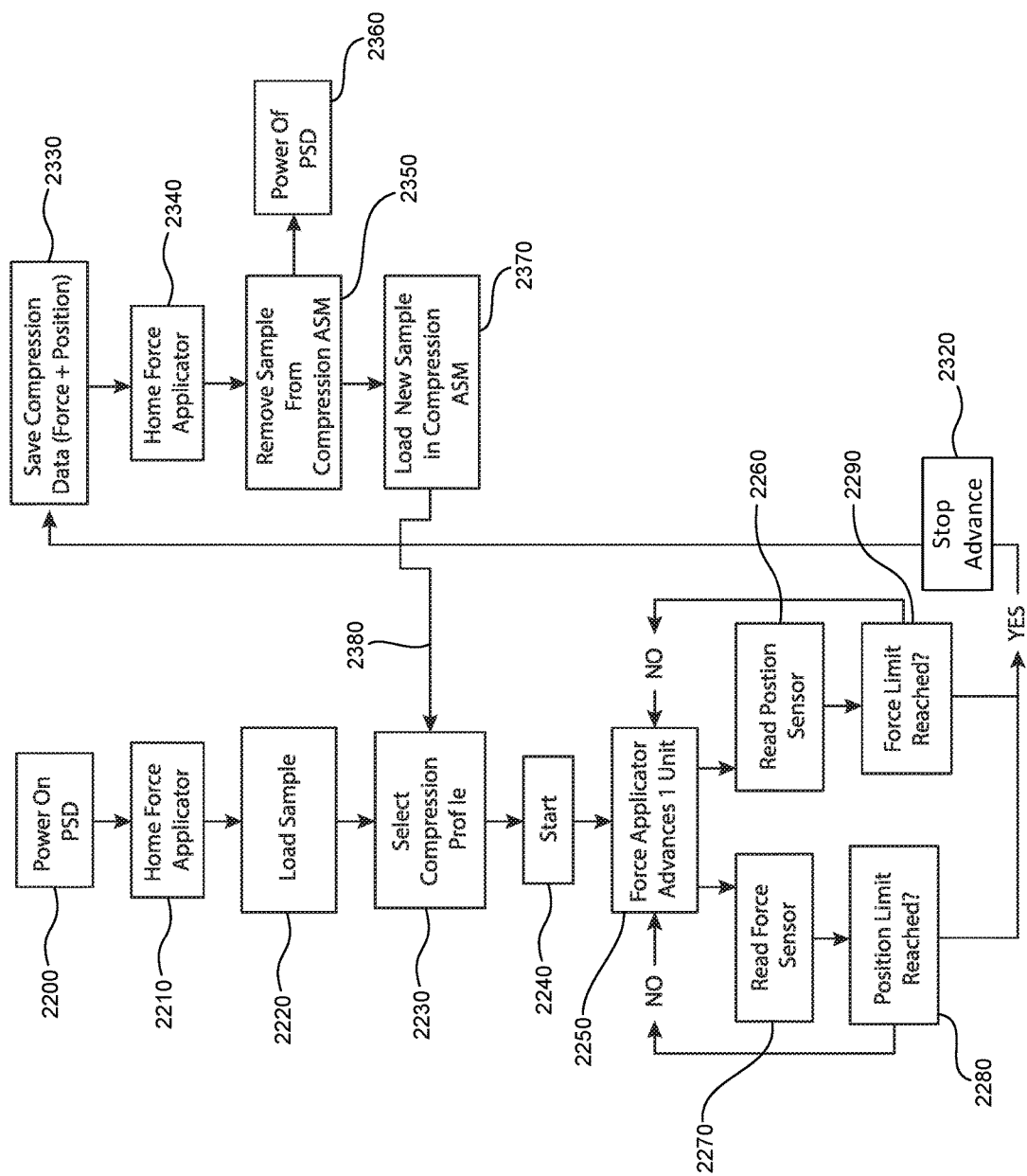
FIG. 11 is a flow chart depicting certain steps in operation of the apparatus of FIG. 10.

An example of an automatic feedback control system which uses both pressure and position is shown in FIG. 11. As shown in FIG. 11, the control system 2100 includes a microcontroller 2140 that linked to a user interface 2160. The user interface 2160 may be any user interface including, but not limited to, a digital display or a series of buttons. The microcontroller 2140 is connected to an actuator 2710 through an appropriate interface 2141 that allows the microcontroller to control operation of the actuator. For example, the interface may include a circuit that supplies electrical power to an electrically powered actuator. The actuator is arranged to apply pressure to a sample in a filtration assembly 2800 that may be an assembly as discussed above, as by moving a force-applying element 2700 such as a ram of a press to move a piston in the filtration assembly. This process is monitored in real time by both a position sensor 2120, which detects the location of the force applicator 2700, and a force sensor 2130, which monitors the degree of force being applied at any given moment. The information collected by these sensors 2120 and 2130 feeds back 150 into the microcontroller 2140, which uses this information to make adjustments to the operation of actuator 2710. The microcontroller 2140 is also connected to a storage apparatus 2170 such as a conventional memory. The memory desirably stores program instructions that can be executed by the microcontroller during operation, and may also store and deliver preset user-selectable settings as well as record data about each use cycle.

FIG. 11 shows a flow diagram of an example of a use cycle of the control system 2100. The use cycle is initiated by powering on the device in step 2200. This begins a process by which the force applicator 2700 is returned to its home position in step 2210. The sample is then loaded in the filtration assembly and secured in place in step 2220. The user then selects user-selectable settings, via the user interface 2160 in step 2230. The user then starts the compression in step 2240. These user-selectable settings define thresholds values for the force to be applied and for the position of force application element 2700. In the next step 2250, the microcontroller signals the actuator 2710 to advance the force application element 2700 one unit of distance, and triggers the force sensor 2130 and pressure sensor 2140 to monitor the progress of the force application element 2700 in steps 2260 and 2270, respectively. In steps 2280 and 2290, the microcontroller determines whether the force exceeds the force threshold and whether the position exceeds the position threshold. As long as the threshold values for position and force are not reached, the microcontroller repeats steps 2250-2290 and the force application element 2700 is advanced. When either of these limits is reached, the microcontroller 2140 halts the motion of the force application element 2700 (step 2320). The microcontroller saves the force and position data from this compression cycle to the storage device 2170 in step 2330. The force application element 2700 is then retracted to the home position in step 2340, after which the sample is removed from the compression assembly in step 2350. The next step is either to power down the unit (step 2360) or load a new sample in the compression assembly (step 2370) and repeat the process (step 380), beginning with step 2230.

Although the controlled compression of the solid elements has been described above in connection with particular apparatus, it is not so limited. For example, controlled compression as discussed above can be applied using a tubular sample receiver having holes in its side walls for discharge of the liquid phase, rather than a filter at the proximal end as discussed above. Such a sample receiver is described in the aforementioned International Application No. PCT/US2016/031743.

Figure 12:
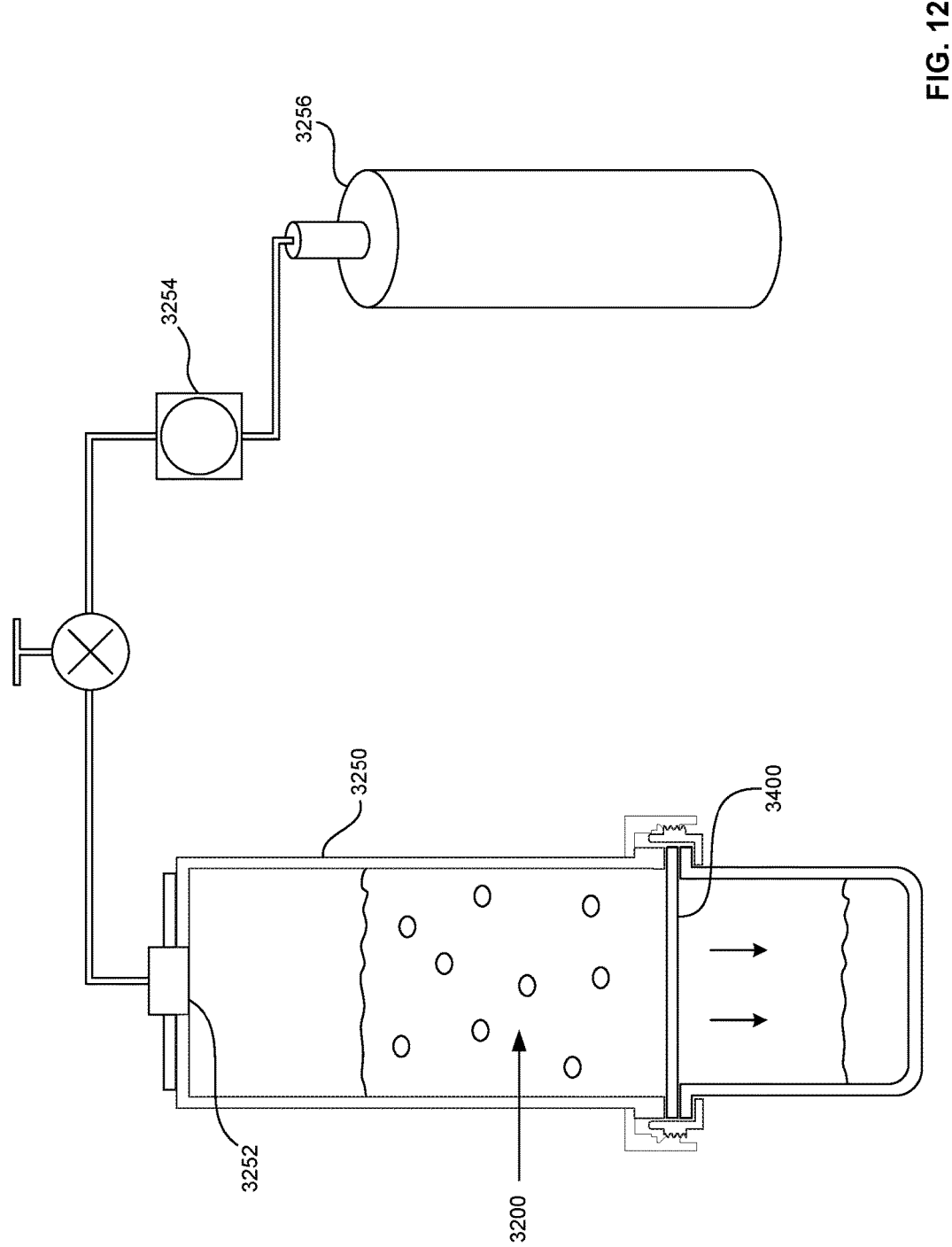
FIG. 12 is a partially schematic, partially sectional view depicting an apparatus according to yet another embodiment of the invention.

In the embodiments discussed above, the means for applying pressure to the sample includes a piston in the sample receiver and means for applying a force to the piston. However, other means can be used to apply pressure to the sample. For example, as shown schematically in FIG. 12, a gas inert to the sample may be introduced into a sample receiver 3250 through a port 3252 disposed above the sample 3200, so as to apply pressure to the sample and force liquid from the sample through a filter 3400. The pressure applied by the gas may be controlled by a gas pressure regulating valve 3254 between a gas source 3256 and port 3252. In a variant of this approach, a piston or a flexible membrane (not shown) may be interposed between the port 3252 and the sample, so as to prevent the gas from penetrating through the sample and the filter.

Figure 13:
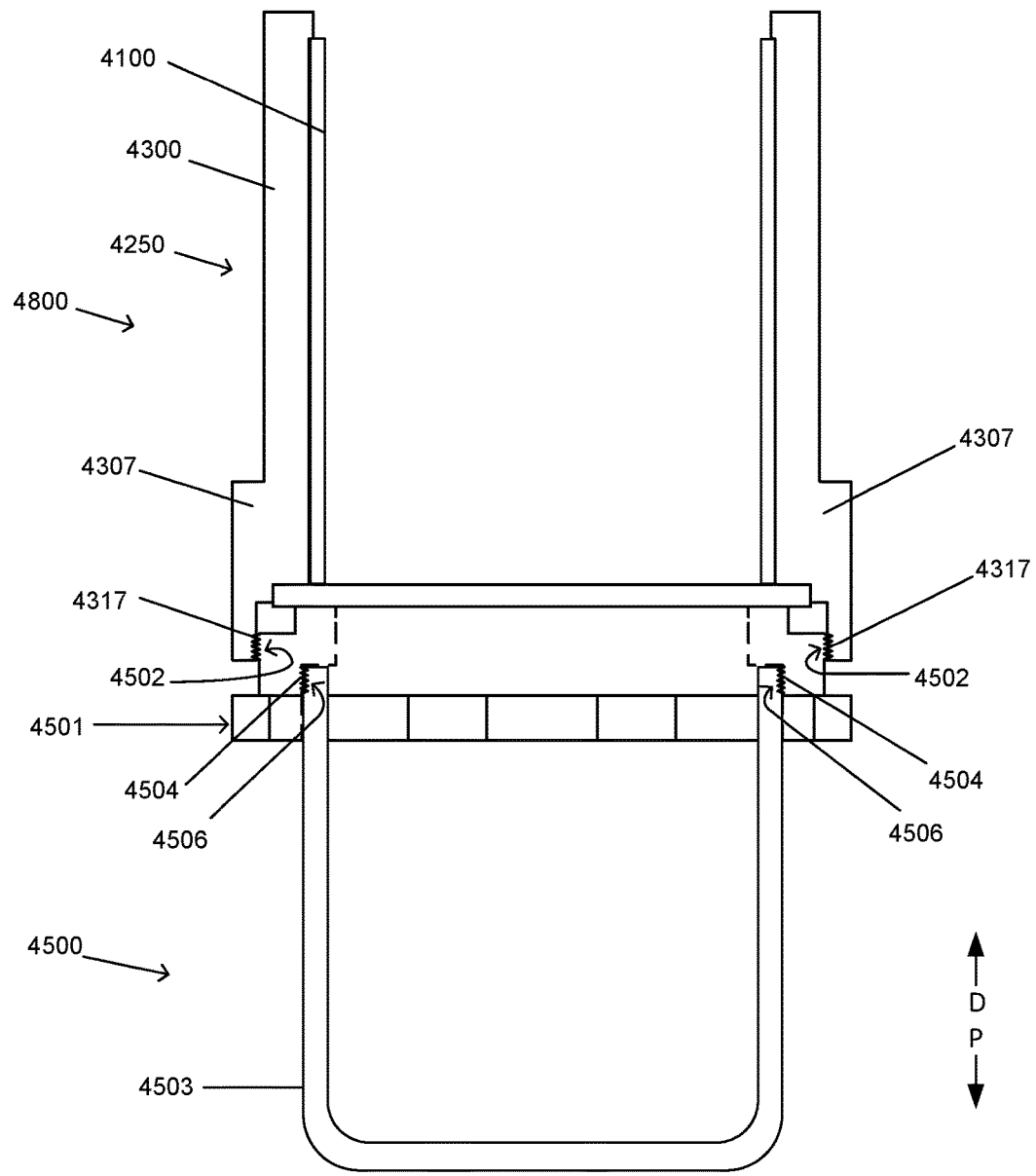
FIG. 13 is a sectional view depicting an assembly according to another embodiment of the invention.

A filtration assembly 4800 (FIG. 13) according to a further embodiment is similar to the filtration assembly discussed above in connection with FIGS. 1-8. In this embodiment as well, the sample receiver 4250 includes an inner element 4100 and a reinforcing sleeve 4300 having attachment elements in the form of a collar 4307 with internal threads 4317. In this embodiment, however, the filtrate receiver 4500 includes a compression ring 4501 bearing attachment features in the form of external threads 4502 adapted to mate with the threads 4317 of the sample receiver. The filtrate receiver 4500 also includes a main element 4503 generally in the form of a cup. The main element is releasably attached to the compression ring. In this embodiment, the ring has internal threads 4504 whereas the main element has external threads 4506. The ring may be formed from a metal, whereas the main element 4503 typically is formed from a polymer. The assembly according to this embodiment is assembled and used in substantially the same way as the assembly of FIGS. 1-8. During the step of assembling the filtrate receiver with the sample receiver, the main element 4503 may be attached to the ring 4501 before or after assembling the ring 4501 with the sample receiver 4502. Ring 4501 may have features (not shown) on its exterior surface which allow engagement of the ring by a wrench.

Figure 14:
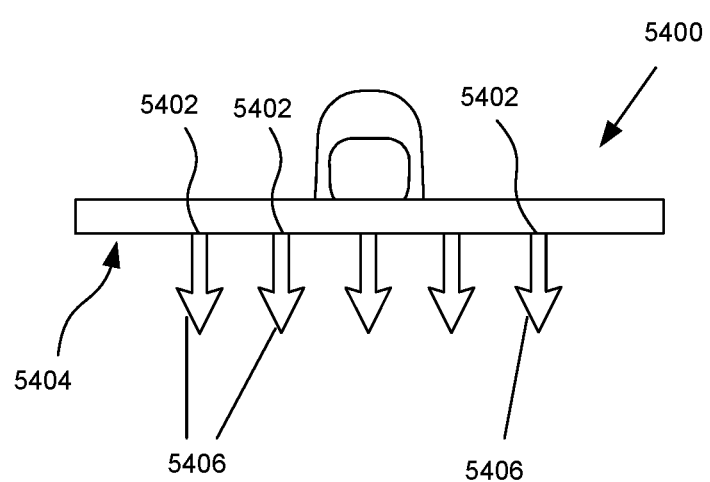
FIG. 14 is a side view depicting a component according to another embodiment of the invention.

In a further embodiment, a filter 5400 (FIG. 14) is provided with pins 5402 projecting from its upstream surface 5404. Each pin may have a head 5406 remote from the upstream surface 5404 of the filter, the head being wider than the remainder of the pin. This filter is used in the same manner as discussed above. When the solid components of a sample are compressed against the upstream surface 5404 of the filter, the pins, including the heads of the pins, are lodged in the compressed solid components. Thus, when the filter is removed from the sample receiver, the compressed solid components will tend to come out of the sample receiver with the filter. The compressed solid components can then be recovered from the filter.

The apparatus and methods discussed herein can be used in applications such as staging of colorectal cancer and ovarian cancer, and in other applications where solid tissues are to be separating from a liquid phase. For example, the compression device could alternatively be used in any applications where fatty tissue needs to be separated. In addition, the apparatus could be used on other types of samples, including, but not limited to, food samples, botanical samples, and artificial substances.

Although the disclosure herein has been described with reference to particular embodiments, it is to be understood that these embodiments are merely illustrative of the principles and applications of the present invention. The paragraphs below further describe certain features of the present disclosure.

The invention claimed is:

1. A method of treating a sample including a solid tissue with a solvent in which fat dissolves to remove at least some of the fat from the solid tissue comprising:
    (a) placing the sample and the solvent in contact with a filter that is placed below the sample and the solvent;
    (b) applying pressure to the sample so as to force the solvent and fat through the filter while retaining the solid tissue on the filter and compressing the solid tissue;
    (c) controlling the pressure-applying step so as to compress the solid tissue to a predetermined degree; and
    (d) recovering the compressed solid tissue.

2. The method according to claim 1, wherein the step of placing the sample in contact with the filter includes placing the sample in a bore of a sample receiver, and securing the filter adjacent a proximal end of the bore so that the sample is disposed between a piston and the filter, and wherein the pressure-applying step pressure includes driving the piston disposed in the bore toward the proximal end and toward the filter.

3. The method according to claim 2, wherein the step of controlling the pressure-applying step includes controlling the magnitude of a force applied to the piston to drive the piston toward the proximal end.

4. The method according to claim 3, wherein the driving step includes operating an actuator to apply the force to the piston, and the controlling step includes monitoring the magnitude of the force and controlling operation of the actuator responsive to the magnitude of the force so that the force does not exceed a predetermined force.

5. The method according to claim 2, wherein the controlling step includes stopping movement of the piston at a predetermined position in the bore, at a predetermined distance from the proximal end.

6. The method according to claim 1, wherein the solid tissue includes lymph nodes.

7. The method according to claim 6, wherein solid tissue includes a section of fatty tissue from the abdomen of a patient having or suspected of having colorectal cancer.

8. The method according to claim 7, further comprising the step of examining the recovered sample so as to derive an indication of the stage of the colorectal cancer.

9. The method according to claim 8, further comprising repeating the aforesaid steps using samples derived from a plurality of patients, while compressing the solid tissue to the same degree in each repetition.

* * * * *